United States Patent [19]
Monti et al.

[11] Patent Number: 5,574,170
[45] Date of Patent: Nov. 12, 1996

[54] KETOROLAC DERIVATIVES WITH CONSIDERABLY REDUCED GASTRO-INTESTINAL IRRITATION AND ULCERATION

[75] Inventors: Carlos E. A. Monti; Gustavo E. Aldoma, both of Buenos Aires, Argentina

[73] Assignee: Roemmers S.A.I.C.F., Argentina

[21] Appl. No.: 468,648

[22] Filed: Jun. 6, 1995

Related U.S. Application Data

[62] Division of Ser. No. 178,541, Jan. 7, 1994, Pat. No. 5,508,301.

[30] Foreign Application Priority Data

Jan. 13, 1993 [DE] Germany .................... 43 00 697.3

[51] Int. Cl.[6] .................................. C07D 209/02
[52] U.S. Cl. ............................................. 548/467
[58] Field of Search ........................... 548/453, 467

[56] References Cited

PUBLICATIONS

Wagner et al Syn Org Chem. (1953) p. 484.

*Primary Examiner*—Alan Siegel
*Attorney, Agent, or Firm*—Webb Ziesenheim Bruening Logsdon Orkin & Hanson, P.C.

[57] ABSTRACT

The present invention concerns compounds of formula (I) which is the novel 2-(1-pyrrolidinyl)ethylester of (±)-5-benzoyl-2,3-dihydro-1H-pyrrolizine-1-carboxyl- or ketorolac-acid, the pharmaceutically acceptable addition salts thereof, preferably oxalate. It is known that the commercially available ketorolac (trometamole salt) exhibits undesired side effects (gastrointestinal irritation and ulceration). Surprisingly, when applying the compounds according to the invention there are considerably less undesired effects which render them potentially of great advantage as analgetic/antiphlogistic agent.

1 Claim, No Drawings

KETOROLAC DERIVATIVES WITH CONSIDERABLY REDUCED GASTRO-INTESTINAL IRRITATION AND ULCERATION

This application is a divisional of U.S. patent application Ser. No. 08/178,541, filed Jan. 7, 1994 now U.S. Pat. No. 5,508,301.

The invention concerns 2-(pyrrolidinyl)ethyl ester of ketorolac or (±)-5-benzoyl-2,3-dihydro-1H-pyrrolizine-1-carboxylic acid, the pharmaceutically acceptable addition salts of these esters, its pharmaceutical composition and use for the preparation of pharmaceuticals to be administered orally or parenterally.

STATE OF THE ART

Non-steroid analgetics/antiphlogistics are commonly used for the treatment of chronic inflammation/irritation diseases, such as arthritis. However, the prolonged administration of these pharmaceuticals exhibits several undesired side effects; the most important are gastro-intestinal irritation and ulceration which represent a still unsolved therapeutical problem.

In regard to the strongest non-steroid analgetics/antiphlogistics of the type derived from aryl acetic or aryl propionic acids it was observed that upon subcutaneous administration the relation between therapeutical effect and undesired side effects is practically the same as with oral administration (the latter being much more convenient for patients). It is assumed that these undesired side effects do not depend on whether the direct contact of the substance with the gastro-intestinal cells takes place in soluble-concentrated or in solid form; rather it depends on the plasma level of the active ingredient (cf. Lombardino (ed.)), *Non-steroidal Antiinflammatory Drugs*; Otterness and Bliven, Chapter 4, pp. 229–230). For that reason it was stated that the esters of these analgetic/antiinflammatory carboxylic acids should not be free of the undesired side effects of the corresponding acids. In fact, these acids are generally commercially available in a free form (e.g. Indometacin, Naproxen, Ketoprofen, Ibuprofen) or in the form of their salts (e.g. Diclofenac sodium salt, Ketorolac trometamole salt) but not in the form of their esters; and as far as the application in the form of esters is proposed these esters are quaternary ammonium salts (e.g. EP 289 262).

In spite of several trials, the need for novel, non-steroid analgetic/antiinflammatory compounds which are characterized by their high therapeutical activity but which irritate the gastro-intestinal tract to a lesser extent and cause less ulcers, has not satisfactorily been met.

DESCRIPTION OF THE INVENTION

The present invention provides a composition of formula (I), the 2(1-pyrrolidinyl)ethyl ester of ketorolac or (±)-5-benzoyl-2,3-dihydro-1H-pyrrolizine-1-carboxylic acid or a pharmaceutically acceptable addition salt of (I), preferably oxalate.

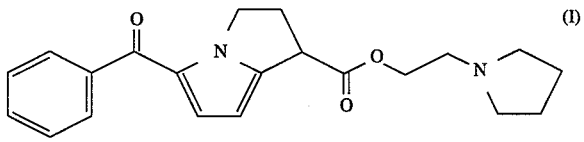

(I)

As is known, the commercially available ketorolac (trometamole salt) causes undesired side effects (gastro-intestinal irritation and ulceration). Surprisingly, the application of the product according to the invention considerably reduces said undesired side effects which makes it potentially a very advantageous analgetic/antiphlogistic.

Subject matter of the present invention is also the 2-(1-pyrrolidinyl)-ethyl ester of ketorolac or a pharmaceutically acceptable addition salt thereof for the therapeutic application, in particular for the treatment of pain or inflammations in human beings and animals.

Moreover, subject matter of the present invention are pharmaceutical compositions including a therapeutically effective amount of 2-(1-pyrrolidinyl)ethyl-ester of ketorolac or a pharmaceutically acceptable addition salt thereof together with pharmaceutically acceptable excipients, in particular suitable galenic formulations for oral or parenteral administration (comprimates, tablets, coated tablets, capsules, syrups, suspensions, injectable solutions etc.).

Also subject matter of the present invention is a process for the preparation of said compositions including mixing a therapeutically effective amount of the product with the appropriate amount of a pharmaceutically acceptable excipient.

Subject matter of the present invention is also the use of 2-(1-pyrrolidinyl)ethyl ester of ketorolac or a pharmaceutically acceptable salt thereof for the preparation of a pharmaceutical for the treatment of pain in human beings and animals.

Subject matter of the present invention is also a process for the preparation of 2-(1-pyrrolidinyl)ethyl ester of ketorolac including the alkylation of (±)-5-benzoyl-2,3-dihydro-1H-pyrrolizin-1-carboxylic acid with 2-(1-pyrrolidinyl)ethyl chloride or an equivalent alkylating reagent, and optionally the addition of the corresponding acid or base for the formation of the desired addition salt which is isolated by crystallization.

The comparison tests according to table 1 show that the pharmaceutical effect of the oxalic acid salt of 2-(1-pyrrolidinyl)-ethyl ester of ketorolac (B in the table) is similar to that of the ketorolac salt that is the trometamole salt (A in the table) and is used in commercially available formulations. It is surprising vis-a-vis the state of the art that the analgetic/antiphlogistic and antipyretic effects of both products are similar.

It is even more surprising, as show the results of the comparison tests of table 2, that the oxalic acid salt of 2-(1-pyrrolidinyl)ethyl ester of ketorolac (column B) exhibits considerably less undesired side effects than the trometamole salt of ketorolac (column A). It is, thus, observed that the ulceration index with (B) is merely one third of that detected with (A); that in the test of possible injuries of stomach tissue with (B) all animals remain unchanged whereas with (A) all show haemorrhages or necrosis; and that the destruction index of the gastric mucosa with (B) is also considerably lower than with (A). And all this with an acceptable acute toxicity for (A) as well as for (B). The 2-(1-pyrrolidinyl)ethyl ester of ketorolac therefore is potentially more advantageous for the therapy than ketorolac.

The state of the art is void of any indication that the surprisingly low level of undesired side effects can be attributed to the 2-(1-pyrrolidinyl)ethyl ester of ketorolac. This level can more or less be attributed to the presence of the 5-membered pyrrolidine ring, which is important as will be shown in the following.

When instead of the pyrrolidine ring the same atoms are present (with two additional hydrogen atoms), but in open form, the pharmacological effect is practically the same but the advantage of less undesired side effects vanishes. This is shown in column (C) of tables 1 and 2 which give the results of comparison tests for the maleate of 2-(diethylamino)ethyl ester of ketorolac. According to the table the ulceration index of 2-(diethylamino)ethyl ester is twice as high as that of 2-(1-pyrrolidinyl)ethyl ester, and the danger of gastric mucosa injuries is much greater with the former than with the latter.

It is practically the same as with the trometamole salt. A similar effect can be observed if methyl groups are used instead of ethyl groups which is evidenced by the test (not shown in the table) with 2-(dimethylamino)ethyl ester. When instead of a (5-membered) pyrrolidine ring the ring has 6 members, the said advantages will not be obtained either which is evidenced by the test (not shown in the table) with 2-(1-piperidinyl)ethyl ester and with the corresponding 2-(4-morpholinyl)ethyl ester.

The high pharmacological effect and the surprisingly low level of undesired side effects of the 2-(1-pyrrolidinyl)ethyl ester of ketorolac and its pharmaceutically acceptable addition salts compared with ketorolac and its other structurally similar esters (which were prepared for the first time) render the product according to the invention particularly useful and advantageous as an analgetic/antiinflammatory agent.

EXAMPLES

Example 1: Comparison Tests as to the Pharmacological Effect

Table 1 shows the comparison results concerning the analgetic, antiphlogistic and antipyretic effect which were obtained by oral administration of the trometamole salt of (commercially available) ketorolac (A), of oxalate of 2-(1-pyrrolidinyl)ethyl ester of ketorolac (subject matter of the present invention) (B) and of maleate of 2-(diethylamino-)ethyl ester of ketorolac (C=comparative formulation) to a rat.

The analgetic effect was measured by the test of inhibition of the contortions generated by peritoneal administration of 0.1 ml acetic acid (3%).

The antiinflammatory effect was evaluated by the Paw-Edema method in which carragenin (1%) was used and the percentage of the decrease of the volume increase was measured at the Paw of The antipyretic effect was determined by increasing the rat's temperature by means of beer yeast by 20% and the rectal temperature of the rat was measured 5, 6, 7 and 8 hours after the administration. The percentage of increase compared to the comparison sample was measured.

TABLE 1

Comparison of the effects of the three ketorolac derivatives:
(A) Trometamole salt; (B) oxalate of 2-(1-pyrrolidinyl)ethyl ester; (C) maleate of 2-(diethylamino)ethyl ester.

| Property (cf. text) | (A) | (B) | (C) |
| --- | --- | --- | --- |
| Analgetic Effect p.o. of 50 (mg/kg) | 0.32 | 0.36 | 0.35 |
| Antiinflammatory Effect p.o. of 50 (mg/kg) | >5 | >5 | >5 |
| Antipyretic Effect p.o. of 50 (mg/kg) | approx. 3 | >3 | approx. 3 |

Example 2: Comparison Tests as Regards the Undesired Side Effects

Table 2 shows the comparison results concerning acute toxicity, ulceration effect, possible lesions of stomach tissue and destruction of gastric mucosa upon oral administration of (commercially available) ketorolac trometamole salt, oxalate of 2-(1-pyrrolidinyl)ethyl ester of ketorolac according to the invention, and maleate of 2-(diethylamino)ethyl ester of ketorolac (here: comparative formulation) to a rat. The acute toxicity is expressed by $LD_{50}$ and is comparable and acceptable in three cases.

The ulceration effect was determined in three groups of 6 rats each. The three above-mentioned products were administered in dosages of 62.5, 100 and 100 mg/kg p.o., respectively. The ulceration effect was evaluated microscopically by means of an ulceration index which corresponds to the sum of evaluations of each animal, multiplied by the percentage of animals above null, divided by the total number of animals (0=normal; 1=minor haemorrhages; 2=considerable haemorrhages; 3=small ulcus; 4=large ulcus, more than 2 mm; 5=perforated ulcus).

The same animals were examined for the degree of injury probability of stomach tissue by means of a microscopic quantification of different degrees of lesions: no change, haemorrhages, necrosis.

The destruction of gastric mucosa was determined from the contents of gastric mucus as cell protecting factor with the animals treated with compounds A and B, either by one single administration of 100 mg/kg p.o. or by daily administration of 25 mg/kg p.o., repeated for 7 days. For every experiment three groups of 6 rats each were used. One group was the comparison group and the results were expressed in percent reduction vis-a-vis this group.

TABLE 2

Comparison of the side effects of two ketorolac derivatives:
(A) trometamole salt; (B) oxalate of 2-(1-pyrrolidinyl)ethyl ester; (C) maleate of 2-(diethylamino)ethyl ester

| Property (cf. text) | (A) | (B) | (C) |
| --- | --- | --- | --- |
| Acute Toxicity p.o. | | | |
| $LD_{50}$ (mg/kg) in the mouse | 118 | 93 | 198 |
| $LD_{50}$ (mg/kg) in the rat | 105 | 235 | — |
| Ulceration (100 mg/kg) Ulceration Index (max. 500) | 400 | 133 | 263 |
| Possibility of Injuries of Stomach Tissue (in 6 rats, microscopically) | | | |
| animals without changes | 0 | 6 | 1 |
| animals with haemorrhages | 2 | 0 | 0 |
| animals with necrosis | 4 | 0 | 5 |
| (acute) destruction of gastric mucosa; 100 mg/kg) % of decrease vis-a-vis comparison sample | 52 (p<0.05) | 27 n.s. | — |
| (chronic) destruction of gastric mucosa; 25 mg/kg) % of decrease vis-a-vis comparison sample | 31 (<0.05) | 7 n.s. | — |

Example 3: Preparation of the Products

For the preparation of 2-(1-pyrrolidinyl)ethyl ester of ketorolac a mixture of 2.55 g (10 mmol) (±-5-benzoyl-2,3-dihydro-1H-pyrrolizine-1-carboxylic acid (Ketorolac) and 4.2 g sodium carbonate was refluxed for about 30 minutes. Thereafter 2.00 g (15 mmol) 2-(1-pyrrolidinyl)ethyl chloride hydrochloride were added while being refluxed and stirred vigorously for about 15 hours. It was then concentrated by removing the solvent under reduced pressure. The residue was suspended in dichloromethane and washed several times in sodium chloride saturated aqueous solution. The organic phase was dried over sodium sulfate, filtered, and the solvent was evaporated by vacuum distillation. The oil was dissolved in absolute ethanol and by-and-by 1.26 g water-free oxalic acid was added. A yield of 82% of oxalate of 2-(1-pyrrolidinyl)ethyl ester of ketorolac was obtained by crystallization. The melting point after crystallization from ethanol was 167°–169° C.

A yield of 84% of 2-(diethylamin)ethyl-maleic ester of ketorolac was obtained by means of an analogous process wherein the hydrochloride of 2-(1-pyrrolidinyl)ethyl chloride was substituted by hydrochloride of 2-(diethylamino)ethyl chloride and the oxalic acid by maleic acid. After crystallization from acetone it shows a melting point of 90°–92° C.

We claim:

1. A process for the preparation of a compound according to formula (I)

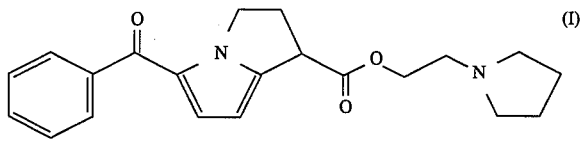

or pharmaceutically acceptable addition salts thereof characterized in that (+)-5-benzoyl-2,3-dihydro-1H-pyrrolizine-1-carboxylic acid is alkylated with 2-(1-pyrrolidinyl)-ethyl-chlorid or a salt thereof.

* * * * *

UNITED STATES PATENT AND TRADEMARK OFFICE
CERTIFICATE OF CORRECTION

PATENT NO. : 5,574,170
DATED : November 12, 1996
INVENTOR(S) : Carlos E. A. Monti and Gustavo E. Aldoma It is certified that error appears in the above-indentified patent and that said Letters Patent is hereby corrected as shown below:

Title page, item '[57] ABSTRACT' Line 2 "ethylester" should read --ethyl ester--.

Title page, item '[57] ABSTRACT' Line 7 "(gastrointestinal" should read --(gastro-intestinal--.

Column 2 Line 12 "ethyl-ester" should read --ethyl ester--.

Column 2 Line 17 after "solutions" insert --,--.

Column 2 Line 31 "pyrrolizin" should read --pyrrolizine--.

Column 2 Lines 37-38 "pyrrolidinyl)-ethyl" should read --pyrrolidinyl)ethyl--.

Column 3 Line 43 "Paw of" should read --paw of the rat.--.

TABLE 2 Column 4 Line 49 after "mg/kg" delete ")".

TABLE 2 Column 4 Line 53 after "mg/kg" delete ")".

Column 4 Line 62 "(±" should read --±--.

Column 4 Line 63 "(Ketorolac)" should read --(ketorolac)--.

UNITED STATES PATENT AND TRADEMARK OFFICE
CERTIFICATE OF CORRECTION

PATENT NO.   : 5,574,170
DATED        : November 12, 1996
INVENTOR(S)  : Carlos E. A. Monti and Gustavo E. Aldoma It is certified that error appears in the above-indentified patent and that said Letters Patent is hereby corrected as shown below:

Column 5 Line 11 "(diethylamin)" should read --(diethylamino)--.

Claim 1 Lines 14-15 Column 6 "pyrrolidinyl)-ethyl-chlorid" should read --pyrrolidinyl)ethyl chloride--.

Signed and Sealed this

Twenty-second Day of April, 1997

Attest:

BRUCE LEHMAN

*Commissioner of Patents and Trademarks*

*Attesting Officer*